(12) United States Patent
Lin

(10) Patent No.: US 8,418,289 B2
(45) Date of Patent: Apr. 16, 2013

(54) AUTOMATED ANTI-SNORING BED SYSTEM

(75) Inventor: Hong-Dun Lin, Taipei (TW)

(73) Assignee: Seda Chemical Products Co., Ltd., New Taipei (TW)

(*) Notice: Subject to any disclaimer, the term of this patent is extended or adjusted under 35 U.S.C. 154(b) by 0 days.

(21) Appl. No.: 13/239,570

(22) Filed: Sep. 22, 2011

(65) Prior Publication Data

US 2012/0324649 A1 Dec. 27, 2012

(30) Foreign Application Priority Data

Jun. 27, 2011 (TW) .............................. 100122472 A

(51) Int. Cl.
*A61G 7/018* (2006.01)
(52) U.S. Cl.
USPC ........................................ 5/613; 5/616; 5/617
(58) Field of Classification Search ........ 5/613, 616–617, 5/715, 915
See application file for complete search history.

(56) References Cited

U.S. PATENT DOCUMENTS

| 7,533,571 | B2 * | 5/2009 | Ariav et al. ..................... 73/597 |
| 2004/0234080 | A1 * | 11/2004 | Hernandez et al. ........ 381/71.11 |
| 2009/0121826 | A1 * | 5/2009 | Song et al. ..................... 340/3.1 |

\* cited by examiner

*Primary Examiner* — Fredrick Conley
(74) *Attorney, Agent, or Firm* — Bacon & Thomas, PLLC

(57) ABSTRACT

The present invention is to provide an automated anti-snoring bed system, which includes a bed designed to support a user lying thereon and internally provided with a driving device, a sensing device able to send out a detection signal toward the user's chest at regular intervals of time and receive a reflected signal returning from the user in response to the detection signal, and a control device. When the sensing device determines that the user is snoring according to the reflected signal, the sensing device sends out a control command to the control device and the control device then drives the driving device to change the configuration of the bed to a mode for stopping the user from snoring. Thus, the user is prevented not only from sleep disorders, but also from sleep apnea which may otherwise jeopardize the user's sleeping quality and health.

3 Claims, 4 Drawing Sheets

AUTOMATED ANTI-SNORING BED SYSTEM

FIELD OF THE INVENTION

The present invention relates to a bed system, more particularly to an automated anti-snoring bed system, which includes a bed, a sensing device, and a control device. The bed is designed to support a user lying thereon and is internally provided with a driving device. The sensing device can send out a detection signal toward the user's chest at regular intervals of time, receive a reflected signal returning from the user in response to the detection signal, and determine whether the user is snoring according to the detection signal and reflected signal. If it is determined that the user is snoring, the sensing device sends out a control command to a control device, and the control device drives the driving device accordingly, so as to change the configuration of the bed to a anti-snoring mode and thereby change the user's sleeping posture with a view to stopping the user from snoring.

BACKGROUND OF THE INVENTION

Most adults sleep about six to eight hours a day, or spend approximately a quarter to a third of each day sleeping. Therefore, the enhancement or improvement of sleeping quality is highly desired. Long-term research results show that many people suffer from sleep disorders, some notable examples of which are insomnia, snoring, sleep apnea, somnambulism, and somniloquy. According to related studies, the probable causes of sleep disorders include stress, a fast pace of life; pain, tobacco, caffeine, alcohol, medication, and so on.

Of all the aforementioned sleep disorders, snoring and sleep apnea draw the most attention from the general public and the medical community. Snoring, which is common among overweight male adults, results from vibration of the edge of the soft palate, and of the secretion of its mucous membrane, when air flows through the upper respiratory tract of someone sleeping. Overweight people are more likely to snore because they tend to have a reduced pharyngeal cavity due to the fat gathering around the throat. Snoring is often accompanied by other symptoms such as drowsiness during the day and headache in the morning. Sleep apnea, on the other hand, refers to shallow or difficult respiration while sleeping and is caused by repeated collapse of the upper respiratory tract (including the nasopharynx, oropharynx, and laryngopharynx) that obstructs the passageway. In severe cases of sleep apnea, complete blockage of the passageway may prevent respiration or even lead to suffocation. While a narrow respiratory tract is attributable to obesity, insufficient muscle strength to maintain free flow in the respiratory tract is also one of the major causes of sleep apnea. In addition, a retruded chin, enlarged tonsils, and an oversized uvula may narrow down the respiratory tract and are responsible for some sleep apnea cases. By medical definition, respiration disorders during sleep can be divided into apnea, which is characterized by pauses of oral and nasal airflow for more than ten seconds, and hypopnea, which is characterized by an at least 50% reduction in pulmonary ventilation volume that lasts for more than ten seconds. The apnea-hypopnea Index (AHI) is composed of the average number of apnea events and the average number of hypopnea events in one hour. Normally, an adult is clinically diagnosed with sleep apnea when his or her AHI has an apnea component greater than five.

It is known from the above that both snoring and sleep apnea are closely related to the breathing condition. Snoring is also generally regarded as a primary symptom of sleep apnea. It is therefore a common goal for the related industry and the medical community to find a way to effectively detect whether someone is snoring and stop the snoring in a timely manner. So far, a snoring sound detector has been successfully developed in Japan. The snoring sound detector has an audio sensor for receiving the user's snoring sound and analyzing the audio signals received, and the user is determined as snoring or otherwise according to the intensity and frequency of the snoring sound. When the snoring sound detector is used, the audio sensor must not be too far away from the user, or the audio sensor will pick up undesirable background noise. Because of that, the user is required to wear the audio sensor around the head, or more specifically on the face, so that the audio sensor is close to the user's nose. However, wearing the audio sensor not only is inconvenient to the user, but also makes the user feel restrained during sleep, which lowers sleeping quality.

Besides, an airflow-based snore detector has been developed in the United States, as shown in FIG. 1. An airflow meter 10 of this snore detector continuously measures the flow of the user's respiration and estimates the user's breathing condition accordingly, thereby determining whether the user is snoring or not. In order to precisely measure the airflow through the user's nostrils, the airflow meter 10 must be secured around the nostrils when the snore detector is used. Additionally, a sensor 11 has to be attached to the user's chest for counting the number of times the user breathes in a predetermined time unit. In other words, snore detection cannot be done without the user wearing the aforesaid devices, which, however, are a source of discomfort and may seriously compromise sleep quality—especially that of those who are more sensitive, if not inviting other sleep disorders.

Aside from the foregoing snore detectors, attempts have been made to apply medical instruments to snore detection. For example, it has been contemplated to detect snoring by means of an electroencephalography (EEG) or electrocardiogram (ECG) monitor. Nonetheless, such professional medical instruments are costly and not suitable for domestic use. Further, in order for the medical instruments to obtain the user's physiological parameters such as heartbeat and respiration rates, electrodes must be attached to the user's body during detection, and yet long-term attachment of the electrodes to the skin may cause skin irritation or even skin lesions. Therefore, the idea of using the aforesaid medical instruments to detect snoring is cost inefficient, potentially harmful to the user's skin, and impractical. Moreover, all the detection devices mentioned above can only detect snoring but cannot stop the users from snoring, which leaves much to be desired.

Hence, the issue to be addressed by the present invention is to overcome the various drawbacks of the conventional snore detectors and design a novel snore detection system which performs non-contact detection to avoid the use of electrodes or audio sensors, and which, upon detecting that the user is snoring, can timely adjust the configuration of a bed so as to effectively stop the user from snoring.

BRIEF SUMMARY OF THE INVENTION

In view of the aforesaid problems of the prior art, the inventor of the present invention conducted extensive research and repeated trials and finally succeeded in developing an automated anti-snoring bed system as disclosed herein. The disclosed system is intended to detect in a non-contact manner whether the user is snoring and to timely adjust the configuration of a bed so that, by changing the user's sleeping posture, the user is stopped from snoring and allowed to have high quality sleep.

It is an object of the present invention to provide an automated anti-snoring bed system which includes a bed, a sensing device, and a control device. The bed is designed to support a user lying thereon and is internally provided with a driving device. The driving device can change the configuration of the bed to a anti-snoring mode or a normal mode. The sensing device can send out a detection signal toward the user's chest at regular intervals of time. The detection signal is reflected upon reaching the user and returns as a reflected signal. The sensing device receives the reflected signal returning from the user, calculates the displacement of the user's chest according to the detection signal and the reflected signal, and determines according to the displacement whether the user is snoring. If it is determined that the user is snoring, the sensing device sends out a control command. The control device receives the control command and drives the driving device accordingly. As a result, the driving device changes the configuration of the bed to the anti-snoring mode and thereby changes the user's sleeping posture, with the intent of stopping the user from snoring. The present invention can change the user's sleeping posture as soon as the user begins to snore, so the user will be effectively stopped from snoring. Thus, the user is prevented not only from sleep disorders but also from sleep apnea which may otherwise jeopardize the user's sleep quality and health. In addition, as the present invention does not require the use of such professional medical instruments as EEG or ECG monitors, the production cost of the disclosed system can be significantly reduced. Moreover, as detection is carried out in the present invention by wireless signal transmission, there is no need to attach electrodes to the user's body or for the user to wear any accessories. Consequently, the discomfort associated with such electrodes and accessories is effectively avoided to ensure the user's sleep quality.

It is another object of the present invention to provide the foregoing automated anti-snoring bed system, wherein the sensing device includes a processor, a signal transmission module, and a signal receiving module. The processor, which is connected to the signal transmission module and the signal receiving module respectively, can drive the signal transmission module to transmit the detection signal. The processor can also obtain the reflected signal via the signal receiving module. Since the present invention implements snore detection by sending out signals and receiving the reflected signals, the user is protected from skin irritation or skin lesions which may otherwise result from the attachment of electrodes to the user's body.

It is still another object of the present invention to provide the foregoing automated anti-snoring bed system, wherein the sensing device further includes a command transmission module. The processor, upon determining that the user is snoring, sends out the control command by way of the command transmission module. Furthermore, the control device includes a control module and a command receiving module. The control module is connected to the command receiving module and can receive the control command via the command receiving module.

BRIEF DESCRIPTION OF THE SEVERAL VIEWS OF THE DRAWINGS

The structure as well as a preferred mode of use, further objects, and advantages of the present invention will be best understood by referring to the following detailed description of an illustrative embodiment in conjunction with the accompanying drawings, in which.

DETAILED DESCRIPTION OF THE INVENTION

The inventor of the present invention has long been engaged in the research, development, and design of beds. In the process, the inventor has found that many people are bothered by snoring, sleep apnea, and like problems and therefore have poor sleeping quality. Although snoring sound detectors and airflow-based snore detectors have been developed for use by those suffering from snoring problems and sleep apnea, the users must endure the discomfort of wearing audio sensors or other accessories in order for the detectors to work. Moreover, the known snore detectors are configured only for detection but not for improving the snoring condition. While the related industry has endeavored to solve the aforesaid problems, an ideal solution has yet to be found. In consideration of this, the inventor came up with the idea of an automated anti-snoring bed system which applies a long-distance detection technique to the determination of the user's snoring condition, and which can adjust the configuration of a bed accordingly so as to timely change the user's sleeping posture and thereby effectively stop the user from snoring.

Figure 1:
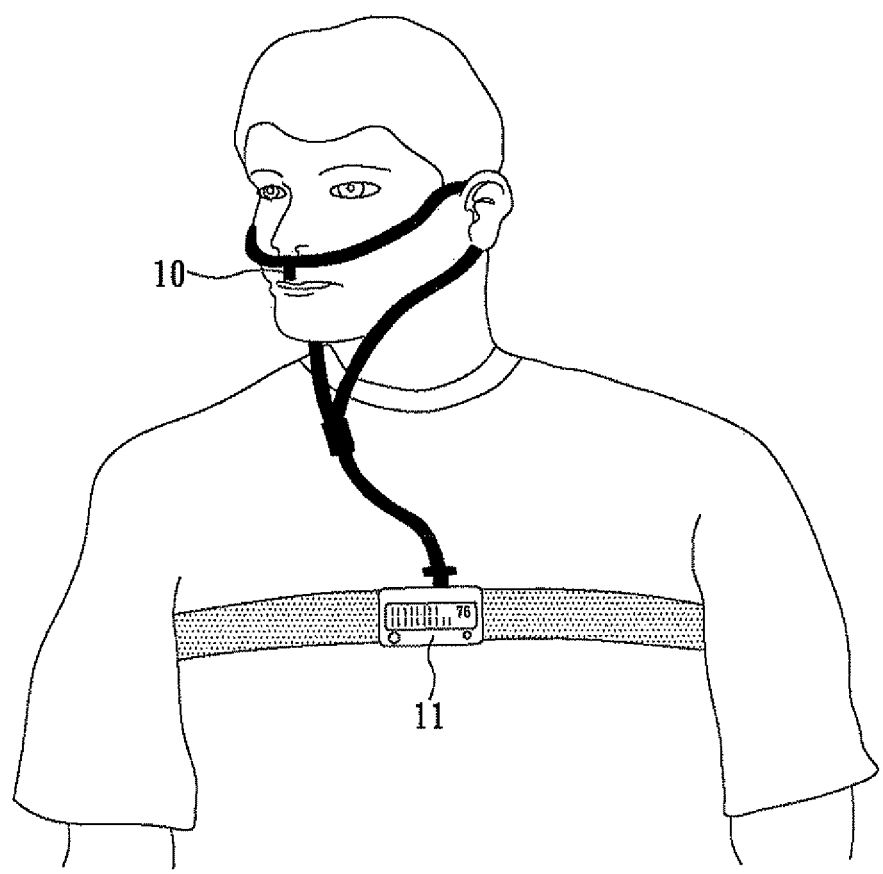
FIG. 1 schematically shows a conventional airflow-based snore detector in use.
Figure 2:
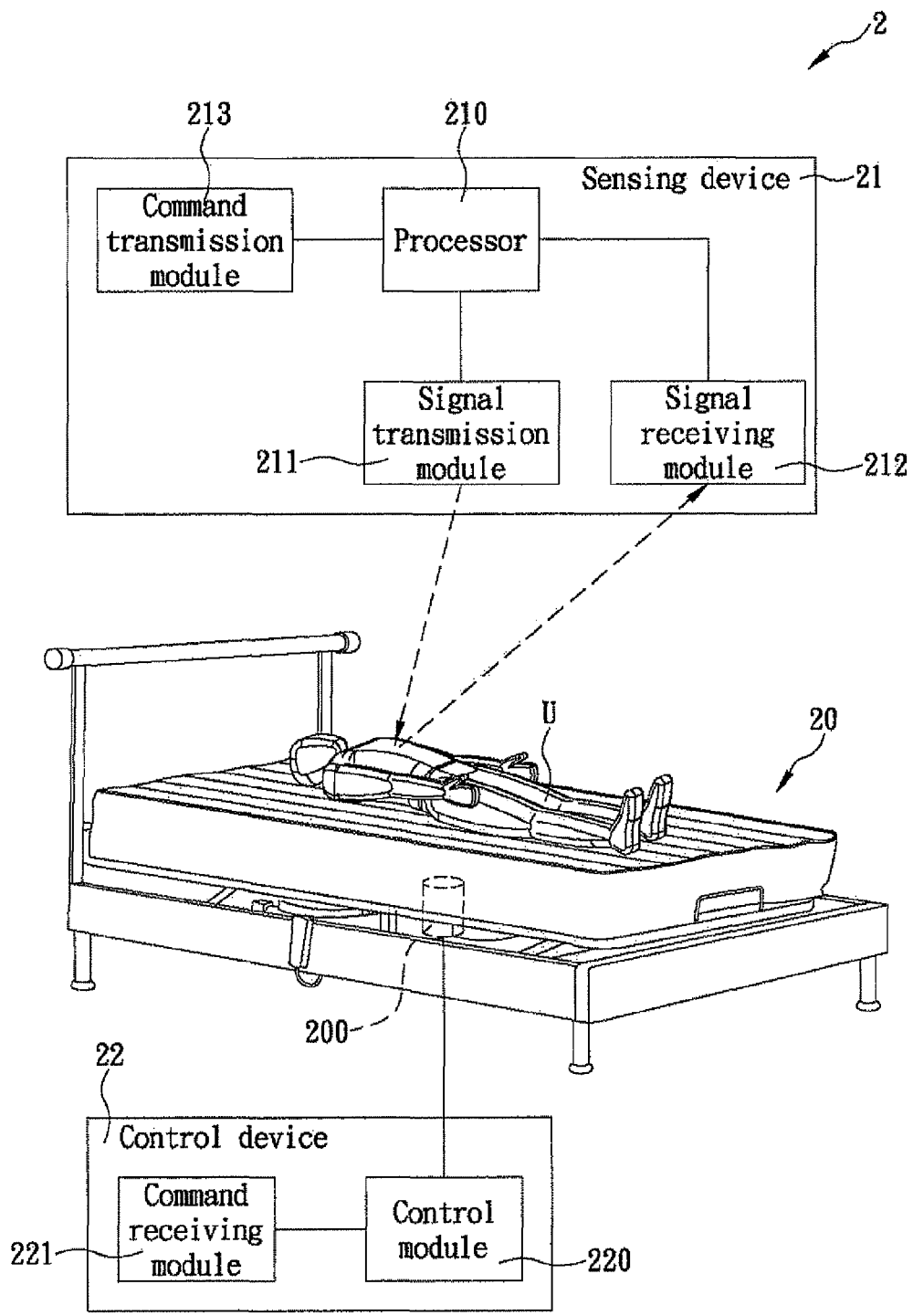
FIG. 2 schematically shows a preferred embodiment of the present invention.

Referring to FIG. 2, an automated anti-snoring bed system 2 according to a preferred embodiment of the present invention includes a bed 20, a sensing device 21, and a control device 22. The bed 20 is designed to support an user U in a lying position and has a driving device 200 installed therein. The driving device 200, which is a motor in this preferred embodiment, is connected to the frame of the bed 20 and configured to change the configuration of the bed 20 to a anti-snoring mode (see FIG. 4) or a normal mode (see FIG. 2). In this preferred embodiment, the driving device 200 can change the curvatures of the bed 20. As the driving principles and the hardware structure of such driving devices are well known in the art of electric beds, and there are a variety of electric bed structures on the market, a detailed description of such principles and structures is omitted herein. Moreover, despite that the driving device 200 in this preferred embodiment is a motor, the present invention imposes no limitations in this regard. For instance, a manufacturer of the system 2 may use other devices (e.g., a pneumatic cylinder, a hydraulic cylinder, etc.) as the driving device 200. All variations easily conceivable by a person skilled in the art should fall within the scope of the present invention.

The sensing device 21 includes a processor 210, a signal transmission module 211, a signal receiving module 212, and a command transmission module 213. The processor 210 is connected to the signal transmission module 211, the signal receiving module 212, and the command transmission module 213 respectively. In this preferred embodiment, the signal transmission module 211 and the signal receiving module 212 are configured for ultra-wideband (UWB) transmission. UWB is a wireless personal area network (WPAN) communication technique that features low power consumption and high data rate. Using pulse signals, rather than continuous sine waves, in signal transmission, UWB is suitable for wireless communication applications requiring high quality services and is applicable to such fields as WPAN, family network connection, and short-range radar. The applicability of UWB to short-range radar is taken advantage of in this embodiment to achieve the intended effects of the present invention.

Figure 3:
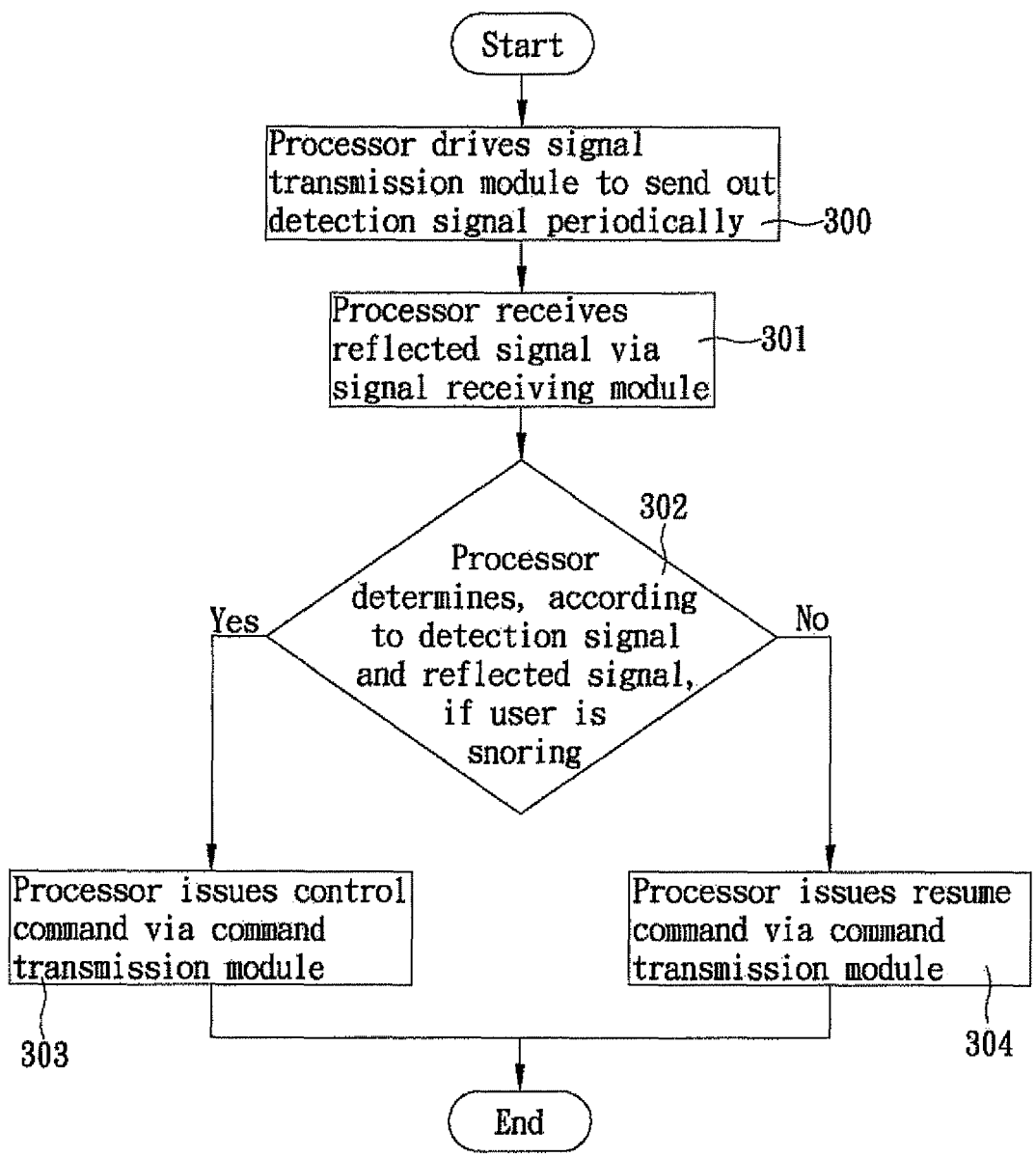
FIG. 3 is a flowchart of the preferred embodiment depicted in FIG. 2.

The processor 210 is configured to drive the signal transmission module 211 so that the signal transmission module 211 sends out a detection signal toward the user U's chest periodically. Once the detection signal reaches the user U, it is reflected and returns as a reflected signal. The signal receiving module 212 receives the reflected signal returning from the user U, so as for the processor 210 to obtain the reflected signal through the signal receiving module 212. Based on the detection signal and the reflected signal, the processor 210 calculates the displacement of the user U's chest (i.e., the extent to which the user U's chest rises and falls) and thereby determines whether the user U is snoring. Upon determining that the user U is snoring, the processor 210 sends out a control command through the command transmission module 213. For better understanding of the technique employed in the present invention, the steps taken by the sensing device 21 are detailed below with reference to FIG. 2 and the flowchart of FIG. 3.

(300) The processor 210 drives the signal transmission module 211 to transmit the detection signal periodically.

(301) The processor 210 receives the reflected signal through the signal receiving module 212.

(302) The processor 210 determines whether the user U is snoring, according to the detection signal and the reflected signal. If yes, step (303) is executed; otherwise, go to step (304).

(303) The processor 210 issues the control command via the command transmission module 213.

(304) The processor 210 issues a resume command via the command transmission module 213.

Figure 4:
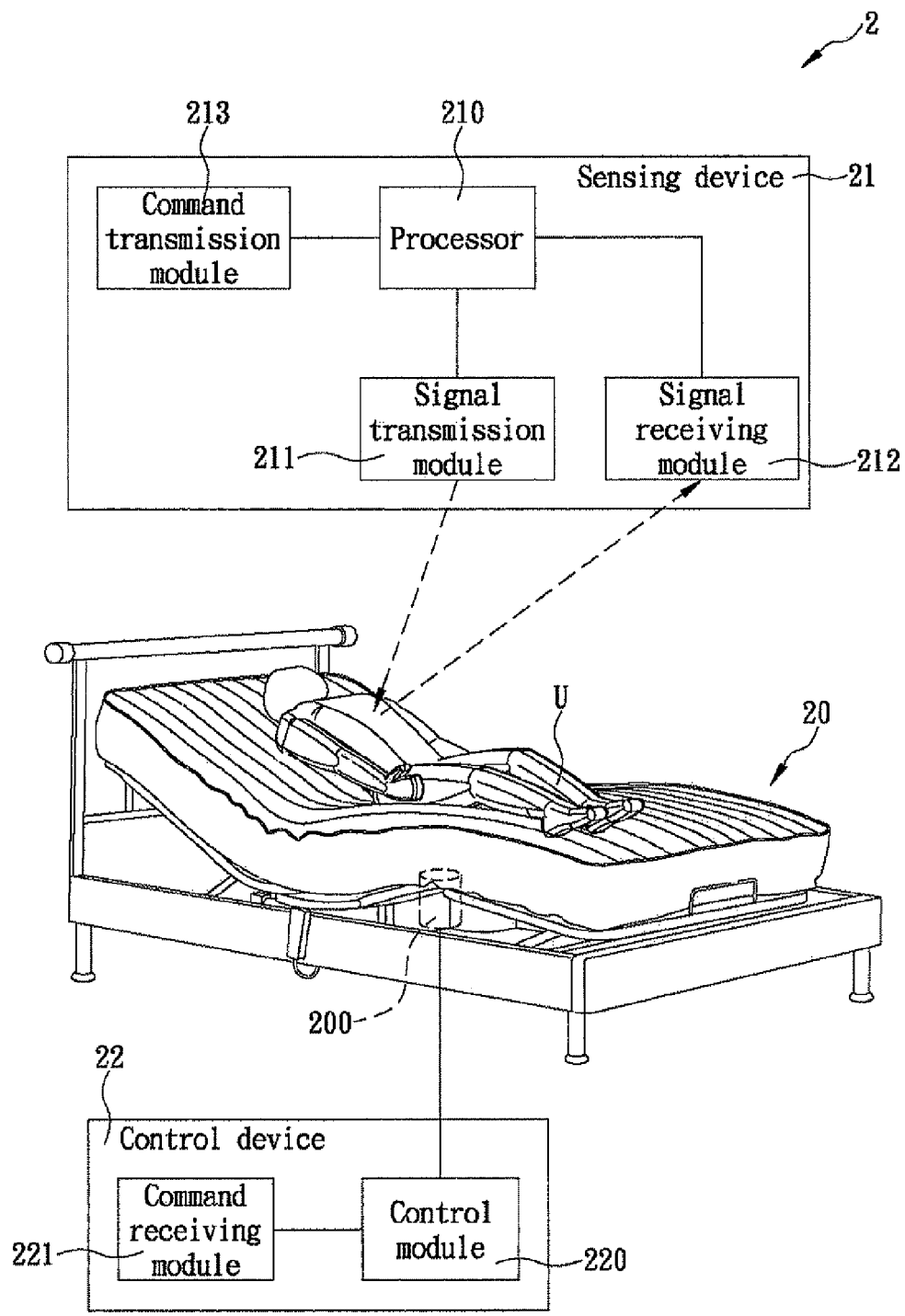
FIG. 4 is another schematic drawing of the preferred embodiment depicted in FIG. 2.

In this preferred embodiment, the control device 22 includes a control module 220 and a command receiving module 221, wherein the control module 220 is connected to the driving device 200 and the command receiving module 221 respectively. In this preferred embodiment, the command receiving module 221 receives the control command by wireless transmission, but the control command can also be received by the command receiving module 221 through other transmission means. For example, when a bed system is made according to the concept of the present invention, the command receiving module 221 and the command transmission module 213 can be connected by a transmission wire without compromising the intended effects of the present invention. All combinations and modifications which are readily conceivable by a person of skill in the art should fall within the scope of the present invention. The control module 220 receives the control command via the command receiving module 221 and drives the driving device 200 according to the control command. Referring to FIG. 4, the driving device 200, once so driven, changes the configuration of the bed 20 to the anti-snoring mode. Thus, the user U's sleeping posture is changed in order to stop the user U from snoring. When the processor 210 subsequently determines, based on the detection signal and the reflected signal, that the user U is no longer snoring—meaning that changing the configuration of the bed 20 has successfully stopped the user U from snoring, a resume command is issued from the processor 210 by way of the command transmission module 213. The control module 220, upon receiving the resume command via the command receiving module 221, drives the driving device 200 to change the configuration of the bed 20 back to the normal mode as shown in FIG. 2, thus allowing the user U to lie flat on the bed 20 again.

According to the present invention, the driving device 200 will not change the configuration of the bed 20 to the anti-snoring mode as long as the user U does not snore. In other words, the user U can sleep in a flat position when not snoring. However, once the user U snores, the detection signal and the reflected signal allow the processor 210 to timely determine that the user U is snoring, so the processor 210 issues the control command. As a result, the driving device 200 is opportunely driven by the control module 220 to change the configuration of the bed 20 to the anti-snoring mode as shown in FIG. 4. In other words, the present invention can change the user U's sleeping posture and thereby stop the user U from snoring immediately when the user U begins to snore. Thus, not only can sleep disorders be effectively prevented, but also the user U's sleep quality and health are kept from being affected by sleep apnea or the like. Since the present invention does not rely on professional medical instruments such as EEG or ECG monitors, the production cost of the system can be substantially lowered. Furthermore, as the user U is detected by means of wireless signal transmission, it is totally unnecessary to attach electrodes (e.g., the ones used in ECG) to the user U's body or for the user U to wear any additional devices (e.g., an audio sensor). As such, the user U can sleep unaffected by the discomfort—and is effectively prevented from skin irritation or skin lesions—which may otherwise result from such electrodes or devices.

While the invention herein disclosed has been described by means of specific embodiments, numerous modifications and variations could be made thereto by those skilled in the art without departing from the scope of the invention set forth in the claims.

What is claimed is:

1. An automated anti-snoring bed system, comprising:
    a bed for supporting a user lying thereon, wherein the bed is internally provided with a driving device configured for changing a configuration of the bed to a anti-snoring mode or a normal mode;
    a sensing device for transmitting a detection signal toward the user's chest periodically, wherein the sensing device isn't in contact with the user's body and comprises a processor, a signal transmission module, a signal receiving module and a command transmission module, the signal transmission module and the signal receiving module are configured for ultra-wideband transmission and for detecting a displacement of the user's chest within every certain period of time, the processor is connected to the signal transmission module and the signal receiving module respectively and is configured for driving the signal transmission module to transmit the detection signal and obtaining a reflected signal through the signal receiving module, and the processor issues a control command through the command transmission module when determining that the user is snoring or in sleep apnea; thereby, when the detection signal is reflected and returns as the reflected signal after reaching the user, the processor calculates a displacement the displacement of the user's chest according to the detection signal and the reflected signal and determines whether the user is snoring or in sleep apnea and then, according to the displacement, issues the control command when it is determined that the user is snoring or in sleep apnea; and
    a control device connected to the driving device, wherein the control device is configured for receiving the control command and driving the driving device according to the control command such that the driving device changes the configuration of the bed to the anti-snoring mode and thereby changes the user's sleeping posture.

2. The automated anti-snoring bed system of claim 1, wherein the control device comprises a control module and a command receiving module, the control module being connected to the command receiving module and configured for receiving the control command through the command receiving module.

3. The automated anti-snoring bed system of claim 2, wherein the control module is connected to the driving device and configured for driving the driving device according to the control command so as to change the configuration of the bed to the anti-snoring mode.

* * * * *